United States Patent [19]

Sullivan

[11] Patent Number: 5,050,798
[45] Date of Patent: Sep. 24, 1991

[54] STATIC AIR FRESHENER DEVICE AND CARTRIDGE

[75] Inventor: William E. Sullivan, Blythewood, S.C.

[73] Assignee: Ecolab Inc., St. Paul, Minn.

[21] Appl. No.: 406,463

[22] Filed: Sep. 13, 1989

[51] Int. Cl.$^5$ .............................................. A61L 9/04
[52] U.S. Cl. ........................................ 239/58; 239/55; 239/57; 221/66
[58] Field of Search .................. 239/44, 45, 47, 49, 239/51.5, 53, 54, 55, 56, 57, 58, 59; 221/66

[56] References Cited

U.S. PATENT DOCUMENTS

| | | | |
|---|---|---|---|
| 1,080,716 | 12/1913 | Rand, Jr. . | |
| 1,496,326 | 6/1924 | Schulte . | |
| 1,972,368 | 9/1934 | Alex | 239/55 |
| 3,575,346 | 4/1971 | Roth et al. | 239/57 |
| 3,711,023 | 1/1973 | Smith | 239/55 |
| 3,807,082 | 4/1974 | Hautmann et al. | 239/55 |
| 3,908,905 | 9/1975 | Von Philipp et al. | 239/55 |
| 4,094,119 | 6/1978 | Sullivan | 53/4 |
| 4,229,415 | 10/1980 | Bryson | 239/57 |
| 4,301,095 | 11/1981 | Mettler et al. | 261/30 |
| 4,352,457 | 10/1982 | Weick | 239/45 |
| 4,415,092 | 11/1983 | Boyer | 221/66 |
| 4,477,414 | 10/1984 | Muramoto et al. | 422/125 |
| 4,523,870 | 6/1985 | Spector | 239/55 |
| 4,529,125 | 7/1985 | Sullivan | 239/56 |
| 4,695,434 | 9/1987 | Spector | 239/57 |

*Primary Examiner*—Andres Kashnikow
*Assistant Examiner*—Christopher G. Trainor
*Attorney, Agent, or Firm*—Merchant, Gould, Smith, Edell, Welter & Schmidt

[57] ABSTRACT

An air freshener device (10) is disclosed. The air freshener device (10) includes a cartridge (12) having a housing (16). The housing (16) has a sealed first cavity (26) and a sealed second cavity (28). First fragrance (60) is located within the first cavity (26) and has a first volatility. Second fragrance (62) is located within the second cavity (28) and has a second volatility. First and second cavities (26) and (28) have first and second openings (64) and (66) respectively. First opening (64) is covered by a first removable cover (68) and second opening (66) is covered by a second removable cover (69). Alternatively, a single cover may be used for both openings. When the covers (68) and (69) are removed the fragrances (60) and (62) independently exit their respective cavities (26) and (28). The device (10) includes an outer housing (14) having a front member (70) which includes air passage openings (72). The outer housing (14) has a back member (74) adapted and configured to be mounted on a surface. Top member (78) and bottom member (80) connect front (70) to back (74). Top and bottom members (78) and (80) have openings (82) and (84) which define a slot (86) extending the length of the outer housing (14). The slot (86) is sized and configured to receive the cartridge (12) whereby when the cartridge (12) is expired a second cartridge (98) is inserted into the slot (86) proximate the top member (78) and the second cartridge (98) is moved in the slot (86) toward the bottom member (80), the cartridge (12) moves downward in the slot (86) and is forced out the bottom member (80) by movement of the second cartridge (98). The air passage openings (72) receive air which moves over the cartridge (12) picking up the fragrances (60) and (62) resulting in an air-fragrance mixture which exits the air passage openings (72) thereby allowing dispersion of the fragrances (60) and (62).

24 Claims, 5 Drawing Sheets

STATIC AIR FRESHENER DEVICE AND CARTRIDGE

BACKGROUND OF THE INVENTION

1. Field of the Invention

This invention relates to air freshener devices and cartridges, and more particularly to air freshener devices wherein the evaporation controlled fragrance cartridge, having means for controlling the evaporation of two fragrances of different volatilities, is easily replaced by inserting a refill fragrance cartridge into the air freshener housing which automatically replaces the expired cartridge.

2. Description of the Prior Art

Air freshener devices typically utilize a card or carrier which contains a fragrance to be evaporated. When the fragrance has evaporated, the card is typically removed by reversing the process by which it was inserted or can be removed by other means requiring the user to follow additional procedures. The user must then take additional steps to refill the device. Also, the devices are usually difficult to access if mounted on a surface and thus the entire process can be time consuming and frustrating to the user.

In addition, in some cases air fresheners are designed to disperse a combined fragrance which includes fragrances of high and low volatility. The result of the typical design is that the evaporation of the fragrance of high volatility is much greater the first few days of exposure and thereafter evaporation rapidly falls off. This results in a short lived period when the combined fragrance is disseminated at an optimum level. Therefore, it is desirable to control evaporation of the fragrance.

One example where the evaporation of the fragrance is controlled to allow reproduction of a desired odor is U.S. Pat. No. 3,711,023, issued Jan. 16, 1973 to Dean E. Smith. An air conditioning system is disclosed which releases evaporated volatile substances into the air to produce an odor. The individual compartments from which the odor is to be formed are stored in individual receptacles and the amount of individual components to be released are controllable. The mixing of various components may be controlled by varying the width of the passage way to vary the proportions of the fragrances being mixed. However, the system is not designed to obtain the even rate of evaporation of fragrances of different volatilities.

U.S. Pat. No. 4,477,414 discloses an apparatus for evaporating a solution of varying volatility (the solution contains ingredients of high, middle, and low notes). A certain amount of the volatile liquid is allowed to be evaporated at one time. An evaporative container is used which comprises a container for holding the solution and a water absorbing impregnation element that is fitted to the head of the container and which uses the mechanism of a siphon to supply liquid to be evaporated. The use of a controlled dispenser allows the remaining solution to retain the original mixture of notes. This patent also includes a device wherein the amount of evaporation of the solution absorbed to be released can be controlled by a rotating lid. However, this device does not utilize the volatilities of the fragrances by effectively controlling evaporation through separate cavities.

The present invention addresses the problems associated with the prior art devices and provides an air freshener device that not only controls evaporation thereby allowing optimum prolonged release of the fragrances, but also provides an easy automatic refill system.

SUMMARY OF THE INVENTION

The present invention provides an air freshener device and cartridge for dispersing a desired fragrance into the air. The cartridge includes a housing. The housing has first and second separately sealed cavities. The first cavity contains a first fragrance of first volatility while the second cavity contains a second fragrance of second volatility. Each first and second cavity has an opening and each opening has a removable cover. When the cover is removed, the fragrances independently exit their respective cavities.

The air freshener device includes an outer housing. The outer housing has a front member having air passage openings and a back member which is adapted and configured to be mounted on a surface. The outer housing has top and bottom members connecting front to back. The top and bottom members have openings which define a slot which extends the length of the outer housing. The slot is sized and configured to receive the cartridge.

When the fragrance of the cartridge has evaporated, a second cartridge may be inserted into the slot proximate the top member. When the second cartridge is moved toward the bottom member, the cartridge is forced out the bottom member by the movement of the second cartridge. Therefore, the outer housing is refilled by the second cartridge. The air passage openings of the outer housing receive air which moves over the cartridge picking up the fragrance. The resulting air-fragrance mixture exits the air passage openings thereby allowing dispersion of the fragrance.

DESCRIPTION OF THE PREFERRED EMBODIMENT

Figure 8:
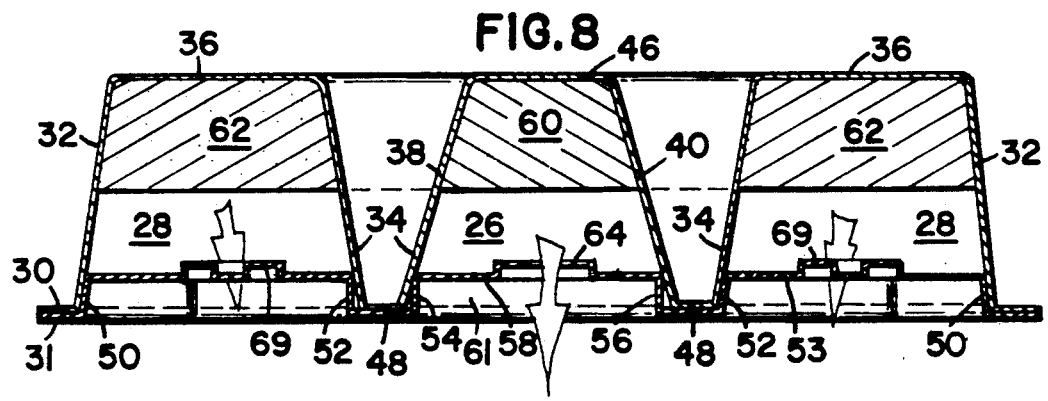
FIG. 8 is a cross sectional view taken generally along the line 8—8 in FIG. 1.

Referring to the drawings, wherein like numbers represent like parts throughout the several views, there is generally disclosed at 10, an air freshener device. The device 10 includes a cartridge 12 and an outer housing 14. The cartridge 12 includes a housing 16. The housing 16 has a leading edge 18 and a trailing edge 20. The housing 16 is generally rectangular except for the two angled portions 22 and 24 at the leading edge 18 which will be described in more detail later in this description. The housing 16 includes a first cavity 26 and a second cavity 28. As shown in FIG. 8, first and second cavities 26 and 28 are separately sealed by membrane 30 cooperatively connected to lid 31. The membrane 30 defines the cavities 26 and 28.

In the preferred embodiment, the membrane 30 is made of a barrier plastic but any suitable material may be used. Membrane 30 has a continuous outer wall 32 which provides the outside boundary for second cavity 28 and a continuous inner wall 34 which provides the inside boundary for second cavity 28. A continuous top wall 36 is generally perpendicular to, positioned between, and connects outer wall 32 and inner wall 34 to form second cavity 28. The second cavity 28 generally forms a ring proximate the outer edges of the housing 16.

Figure 7:
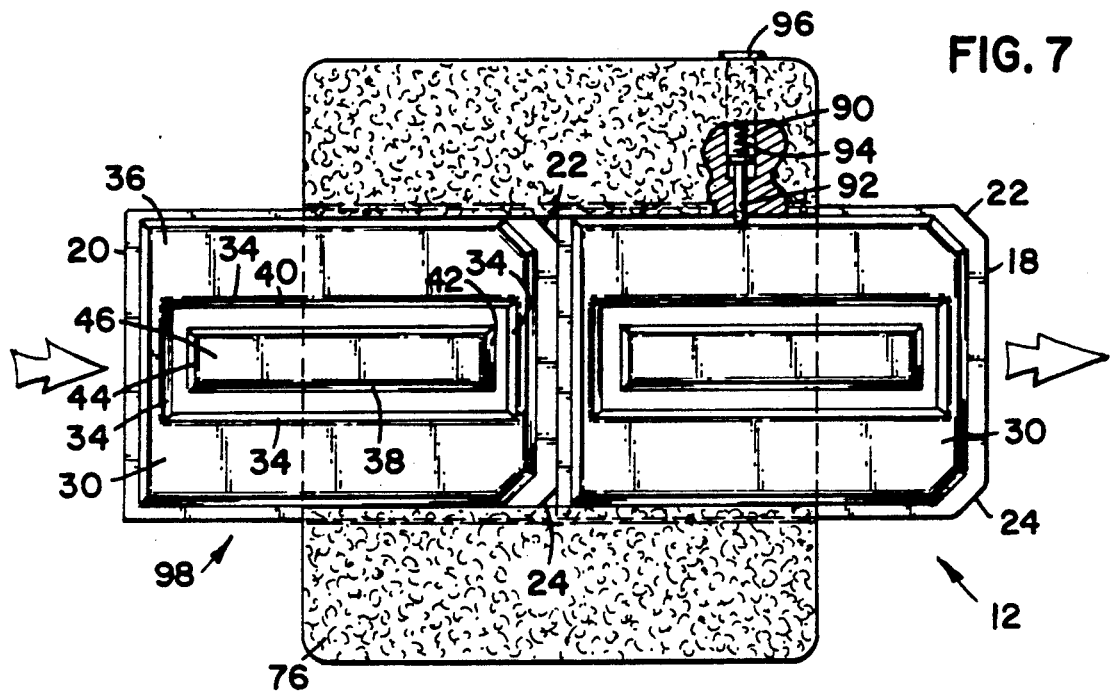
FIG. 7 is a rear view of the device of FIG. 1 showing the refill cartridge entering the outer housing and the exiting of the expired cartridge.

As shown in FIGS. 7 and 8, the first cavity 26 is defined by a first wall 38 and a second wall 40. Front wall 42 and back wall 44 are each positioned between and connected to opposite ends of each first and second walls 38 and 40. Third wall 46 is generally perpendicular to first and second walls 38 and 40, and front and back walls 42 and 44 and connected to form the first cavity 26 having a generally rectangular cross-section. First cavity 26 is sized and configured to fit within the ring formed by second cavity 28. A continuous protrusion 48 provides a space between the cavities 26 and 28 and aids in keeping the cavities 26 and 28 separately sealed. The protrusion 48 can be seen more clearly in FIG. 1. It is to be understood that the configuration of the first and second cavities 26 and 28 need not be as shown, as any other suitable configuration may be used. However, it should be clear that the cavities 26 and 28 must be separately sealed.

Figure 1:
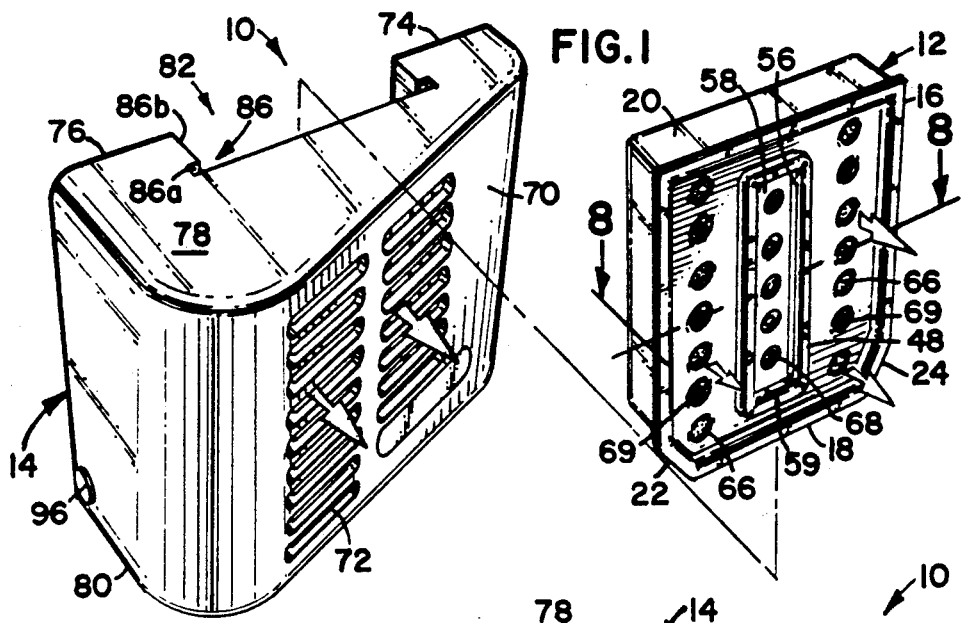
FIG. 1 is an exploded perspective view of the air freshener device incorporating the present invention.

Referring now to FIGS. 1 and 8, the lid 31 is sized and configured to seal and separate cavities 26 and 28. The lid 31 is generally formed to mate with the housing 16. The lid 31 has a continuous outer barrier 50 and a continuous inner barrier 52 which are connected by a continuous top barrier 53 which is generally perpendicular to inner and outer barriers 50 and 52. This portion of lid 31 helps seal the second cavity 28.

The first cavity 26 is sealed in a similar manner. First barrier 54 is positioned parallel to second barrier 56. Front barrier 59 and back barrier 61 are connected to first and second barriers 54 and 56 at opposite ends. The third barrier 58 is generally perpendicular to and connects first, second, front and back barriers 54, 56, 59 and 61 to seal first cavity 26.

First cavity 26 contains first fragrance 60 having a first volatility. Second cavity 28 contains a second fragrance 62 having a second volatility. The first volatility is lower than the second volatility. The first cavity 26 contains a slow evaporating fragrance or base notes while the second cavity 28 contains a fast evaporating fragrance or top notes. Separately sealing the cavities 26 and 28 prevents mixing of the first fragrance 60 and the second fragrance 62 while in their respective cavities 26 and 28.

The lid 31 has a plurality of possible first and second openings 64 and 66 aligned with each of the cavities 26 and 28 thereby providing a possible means for the fragrances 60 and 62 to exit their respective cavities 26 and 28. The openings 64 and 66 are generally circular and are formed as part of the lid 31. The openings 64 and 66 are covered by first and second removable covers 68 and 69. Each removable cover is sized and configured to fit within the openings 64 and 66 and are therefore, generally circular. The removable covers 68 and 69 must be removed by the end user in order for the fragrances 60 and 62 to escape their respective cavities 26 and 28. The removable covers 68 and 69 are removed by pressing them in toward the cavities 26 and 28 thereby breaking the seal between the covers 68 and 69 and the lid 31. When the removable covers 68 and 69 are removed, the fragrances 60 and 62 are free to independently exit their respective cavities 26 and 28.

The use of a larger volume of fast evaporating top notes in the second cavity 28 and a smaller volume of slow evaporating base notes in the first cavity 26 allows equalization of the time periods for which the evaporation is optimal. The slow evaporating base notes have a greater number of openings 64 allowing for greater evaporation while the top notes have less openings 66. This control of evaporation allows for an air freshener with superior performance.

The determination of how many openings each cavity should have is governed by the volatilities of the two fragrances, the volumes of the two fragrances, and the desired results. Different results can be reached with different combinations. For example, using a larger volume of base notes and a smaller volume of high notes will result in different rates of evaporation depending on the area exposed by the openings. It may be that a larger volume of base notes in combination with a smaller volume of top notes will result in optimal equilibrium for a particular fragrance. A greater number of openings in the base note cavity will produce a different result than if the high note cavity had a greater number of openings.

Figure 9:
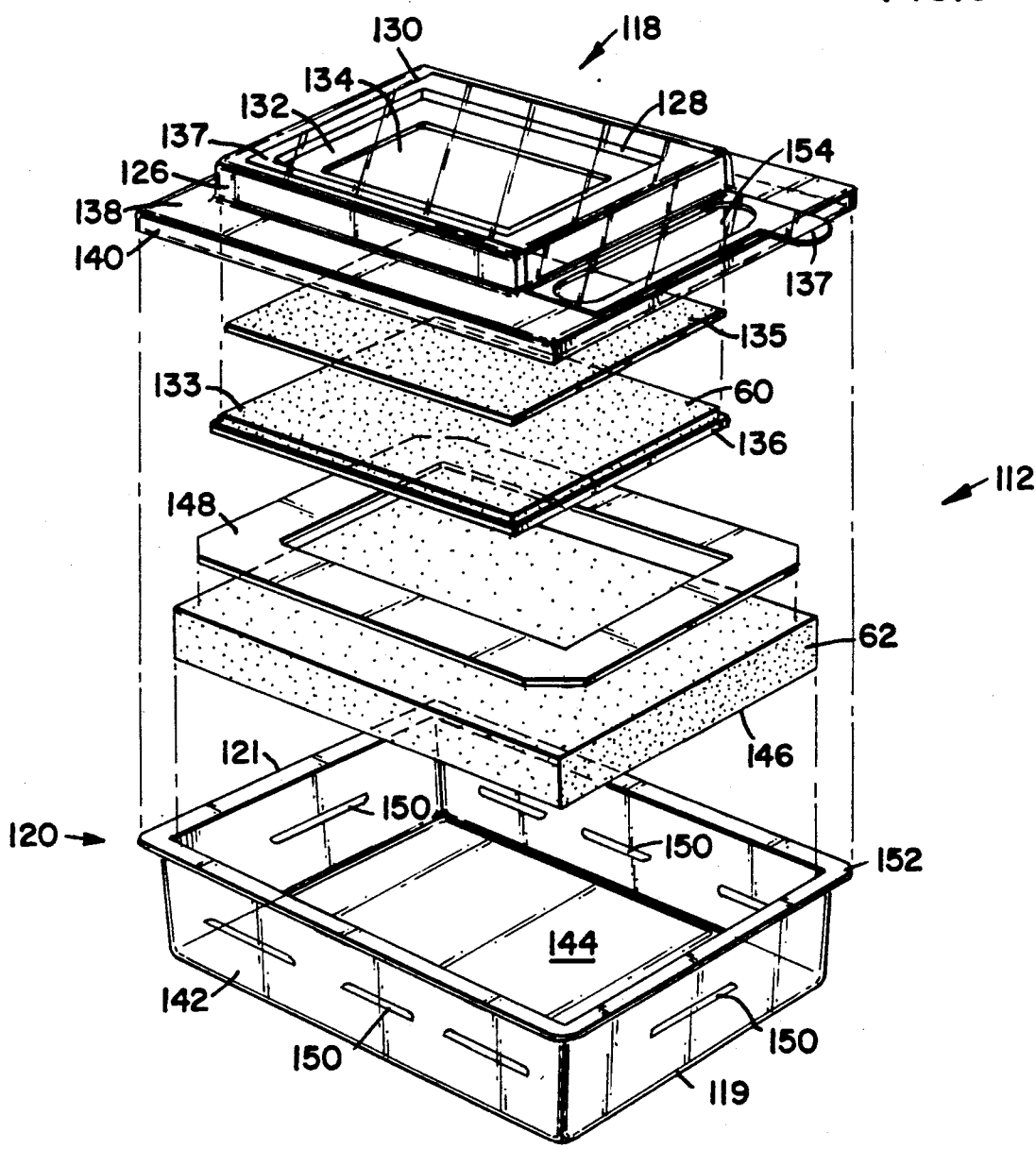
FIG. 9 is an exploded perspective view of another embodiment of the cartridge of the present invention.

Referring now to FIG. 9, an alternative preferred embodiment for the cartridge is shown. The cartridge 112 has a leading edge 119 and a trailing edge 121. The first cavity 118 is formed by a continuous outer wall 126, continuous inner wall 128, top wall 130, and wall 132. Continuous outer wall 126 provides the outside boundary for the first cavity 118. Continuous outer wall 126 and continuous inner wall 128 are generally parallel to each other and both are generally perpendicular to top wall 130 and wall 132. Top wall 130 and wall 132 are connected by inner wall 128. These walls 126, 128, 130, and 132 are formed as a single integral unit or first cavity 118. First fragrance 122 is contained in a pad 133 in the preferred embodiment. A diffuser 135 is placed on top of pad 133 to maintain the position, surface, and placement of pad 133, as well as, to act as a diffuser. Pad 133 is made of a non-woven polyester in the preferred embodiment, although it should be understood that any other suitable material may be utilized. The fragrance from pad 133 wicks into diffuser 135 and evaporates from it. The diffuser 135 is made of spun bonded polyester in the preferred embodiment.

Wall 132 is shown with a selectable opening 134 in FIG. 9. The opening 134 is generally rectangular in the preferred embodiment and approximately measures 2⅛ inches by 2⅜ inches. The opening 134 is necessary to allow the first fragrance 60 to escape the cartridge 112. The end user will remove a cover 137 which is sized and configured to fit within or cover the opening 134 and connected to first cavity 118 by an adhesive to allow the first fragrance 60 to escape the sealed first cavity 118.

First cavity 118 is separately sealed from second cavity 120 by membrane 136. A lid 138 generally perpendicular to and connected to outer wall 126 in conjunction with membrane 136 seals the first cavity 118 from second cavity 120. A continuous first lip 140 which is generally perpendicular to and connected to lid 138 aids in separately sealing the cavities 118 and 120 which will be discussed in further detail later in this description. Membrane 136, lid 138 and first lip 140 form a single integral unit with first cavity 118. Membrane 136 is a barrier film and is made of a PET film in the preferred embodiment.

Second cavity 120 is formed by a continuous first wall 142 connected to a bottom wall 144. The first wall 142 forms the outside boundary for second cavity 120. The bottom wall 144 is generally perpendicular to the first wall 142 and the connection of these walls 142 and 144 forms the cavity 120. First wall 142 and bottom wall 144 are formed as a single unit or second cavity 120.

The second fragrance 62 is placed in pad 146 in the preferred embodiment and is located in the second cavity 120. The pad 146 is a non-woven polyester in the preferred embodiment. Retainer 148 is placed on the fragrance 62 and pad 146 to hold them in place. The retainer 148 generally forms a ring proximate the continuous first wall 142. The retainer 148 fits under and is kept in place by protrusions 150 in the first wall 142. The retainer 148 is constructed of PET film in the preferred embodiment.

A continuous second lip 152 is formed integrally with the first continuous wall 142 to aid in separately sealing the cavities 118 and 120. First lip 140 is generally formed to mate with second lip 152 to form the cartridge housing 116 which comprises first cavity 118 and second cavity 120. First lip 140 of the first cavity 118 is placed over second lip 152 to form a seal between the cavities 118 and 120. A selectable second opening 154 in the lid 138 provide a means for the second fragrance 62 to escape into the environment. The opening 154 is generally rectangular in the preferred embodiment and approximately measures 2⅜ inches by ⅝ inches. The end user will remove cover 137 from the openings 154 to allow the second fragrance 62 to escape the sealed second cavity 120.

As previously discussed, the wall 132 has a selectable opening 134 aligned with cavity 118 while lid 138 has selectable second openings 154 aligned with second cavity 120 thereby providing a means for the fragrances 60 and 62 to exit their respective cavities 118 and 120. The openings 134 and 154 are covered by a removable cover 137. Cover 137 is utilized to retain the fragrances 60 and 62 until the end user removes the cover 137 for use. The removable cover 137 is sized and configured to cover the openings 134 and 154. In the preferred embodiment, the removable cover 137 must be removed by the end user in order for the fragrances 60 and 62 to escape their respective cavities 118 and 120. The removable cover 137 is peeled off of the cartridge housing 116 where it is attached by an adhesive, thereby exposing the openings 134 and 154. Therefore, when the cover 137 is removed, the fragrances 60 and 62 are free to independently exit their respective cavities 118 and 120. In the preferred embodiment, a barrier plastic is heat sealed to the cartridge 114. It should be understood that any other size, configuration or material of cover 137, including separate covers for each opening, may be utilized.

Figure 10:
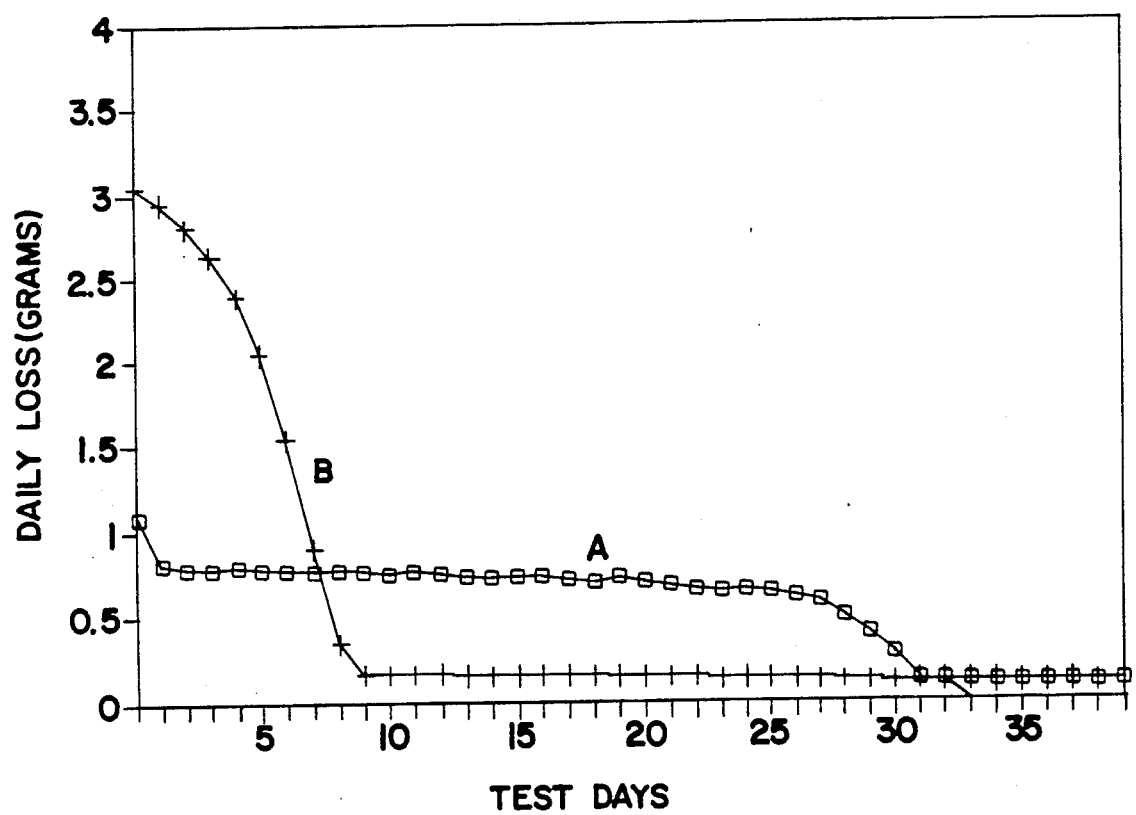
FIG. 10 is a graph illustrating the daily evaporation of the cartridge of the present invention.

Referring now to FIG. 10, an example of the fragrance weight loss for fragrances placed in the cartridge 112 discussed above and shown in FIG. 9 is illustrated. A total of eighteen (18) grams of cherry top notes, comprised of 16.2 grams of benzaldehyde and 1.8 grams of BHT were placed in second cavity 128. Four (4) grams of cherry base notes, comprised of 3.8 grams of EMP glicidate (alderhyde C16) and 0.2 grams of BHT were placed in first cavity 126. Line A in FIG. 10 illustrates the daily evaporation of these split note, separately sealed fragrances. For comparison, a total of 22 grams of top and base notes were mixed and placed in the same embodiment of cartridge 112. The mixed fragrance included 16.2 grams of benzaldehyde, 3.8 grams of EMP glicidate (alderhyde C16) and 2.0 grams of BHT. Four (4) grams of the mixture were placed in base note reservoir or first cavity 126 and eighteen grams of the mixture was placed in second cavity 128. Line B of the graph of FIG. 10 illustrates the rapid evaporation of the mixed note fragrances. Almost all of the fragrance had evaporated by the tenth day. However, the split note fragrances of the present invention demonstrated controlled evaporation of approximately 0.8 grams per day for an extended period of time.

The volatilities of top notes and base notes may be significantly different. For example, the volatility of Benzaldhyde (1100 microns at 25° C.) compared to the volatility of Ethyl Vanallin (0.15 microns at 25° C.) has a volatility ratio of over 7000 to 1. The following table provides further examples of volatilities of top notes and base notes.

|  | Fraqrance Inqredient | Vapor Pressure in Microns at 25° Centigrade |
| --- | --- | --- |
| Top Notes | Benzaldhyde | 1100 |
|  | Spearmint oil | 250 |
|  | Limonene | 950 |
|  | Pinenedle oil Siberian | 580 |
|  | Methyl Salicylate | 118 |
| Base Notes | Citral | 58 |
|  | Carvone | 95 |
|  | Ethyl Vanallin | 0.15 |
|  | Emp Glicidate | 3 |

The outer housing 14 includes a front member 70 which has a number of air passage openings 72 and a back member 74 which is adapted and configured to be mounted on a surface. In the preferred embodiment, the device 10 is made of wood and is mounted on the back of a door. The air passage openings 72 are generally rectangular in shape but any appropriate shape could be utilized. In the preferred embodiment, Velcro ® 76 is used as a mounting material but it should be understood that any other suitable mounting means would suffice. As seen in FIG. 7, either the pile or hook of the Velcro ® 76 is attached to the back member 74 of the outer housing 14. The remaining material (not shown) is fastened to the back of a door or other suitable surface. Thus, the air freshener device 10 is easily mounted.

Top member 78 and bottom member 80 cooperatively connect front member 70 to back member 74. Top member 78 has a top opening 82 and bottom member 80 has a bottom opening 84 which are sized and configured to form a slot 86 to receive the cartridge 12. The slot 86 extends from the top member 78 to the bottom member 80 thereby extending the length of the entire outer housing 14. In the preferred embodiment, the slot 86 is generally T-shaped. The slot is wider at 86a to receive the edge of the housing 16 of the cartridge 12. The slot 86 is narrower at 86b where the cavities 26 and 28 fit. The slot 86 is designed to receive cartridge 12. Therefore, if the embodiment illustrated in FIG. 9 is utilized, the slot 86 is sized and configured to receive that embodiment including cavities 118 and 120. However, the device 10 operates in the same manner described herein.

A cartridge retainer 88 is located proximate the slot 86. A cylindrical void 90 is located in back member 74 proximate the bottom member 80. The cylindrical void 90 extends from the outer edge of the outer housing 14 to the inside of the slot 86. The cylindrical void 90 holds the cartridge retainer 88 which includes a stop 92, a spring 94 and a plug 96. The plug 96 caps the cylindrical void 90 at the outer edge of the housing 16. The spring 94 is axially aligned and positioned adjacent to the plug 96. The spring 94 is axially aligned and positioned adjacent the stop 92. When the spring 94 is not compressed the stop 92 extends into the slot 86. In this position, the stop 92 acts as a support and cartridge retainer.

Figure 2:
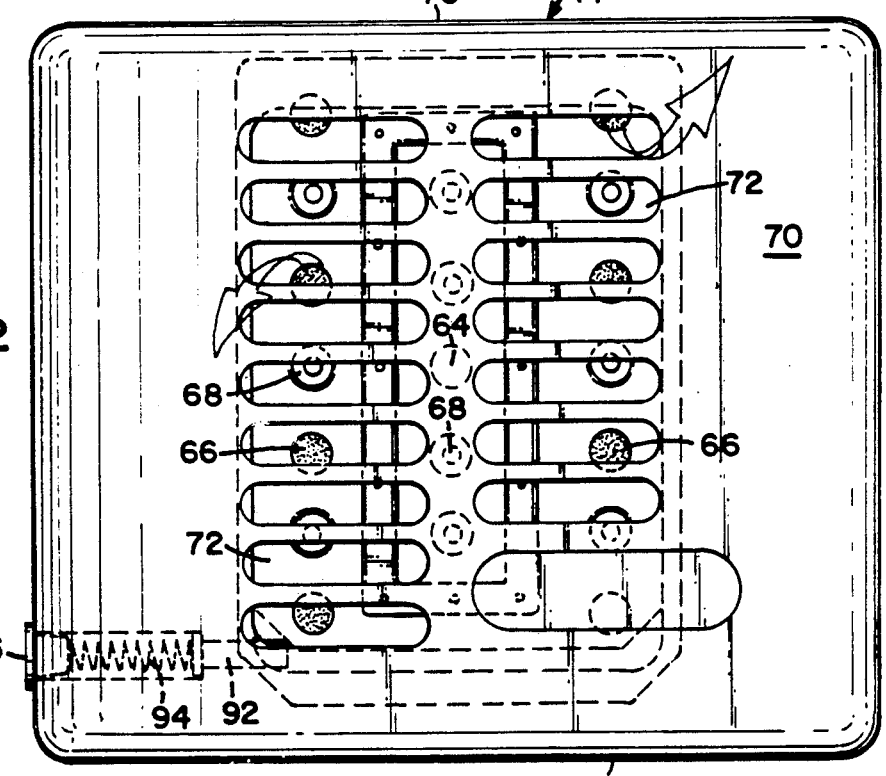
FIG. 2 is a front elevational view of the device of FIG. 1.
Figure 3:
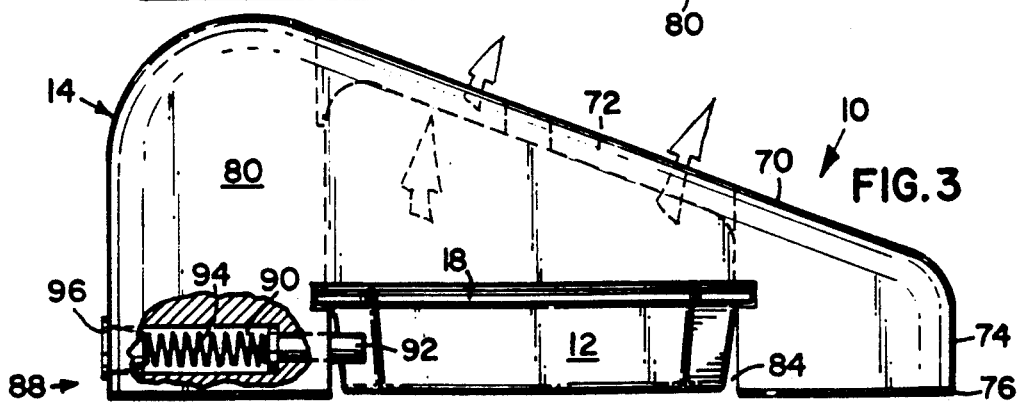
FIG. 3 is a bottom plan view of the device of FIG. 1.
Figure 4:
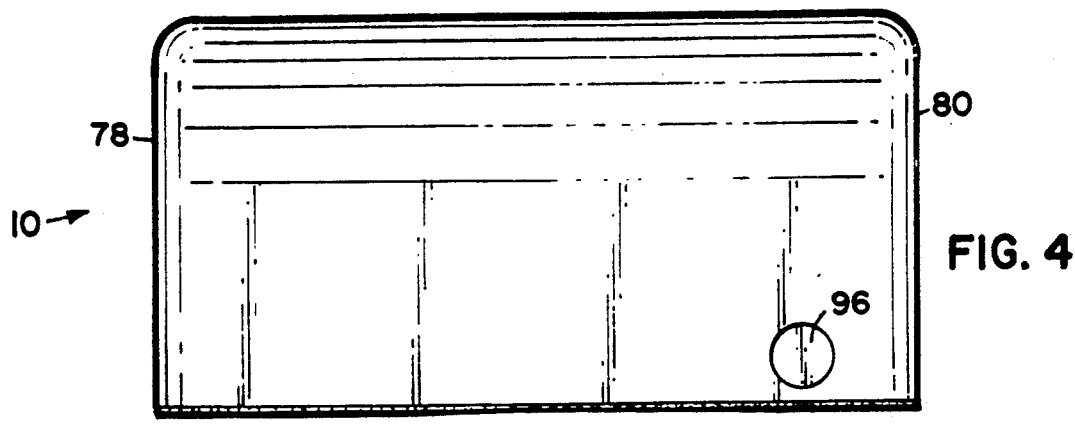
FIG. 4 is a left side elevational view of the device of FIG. 1.
Figure 5:
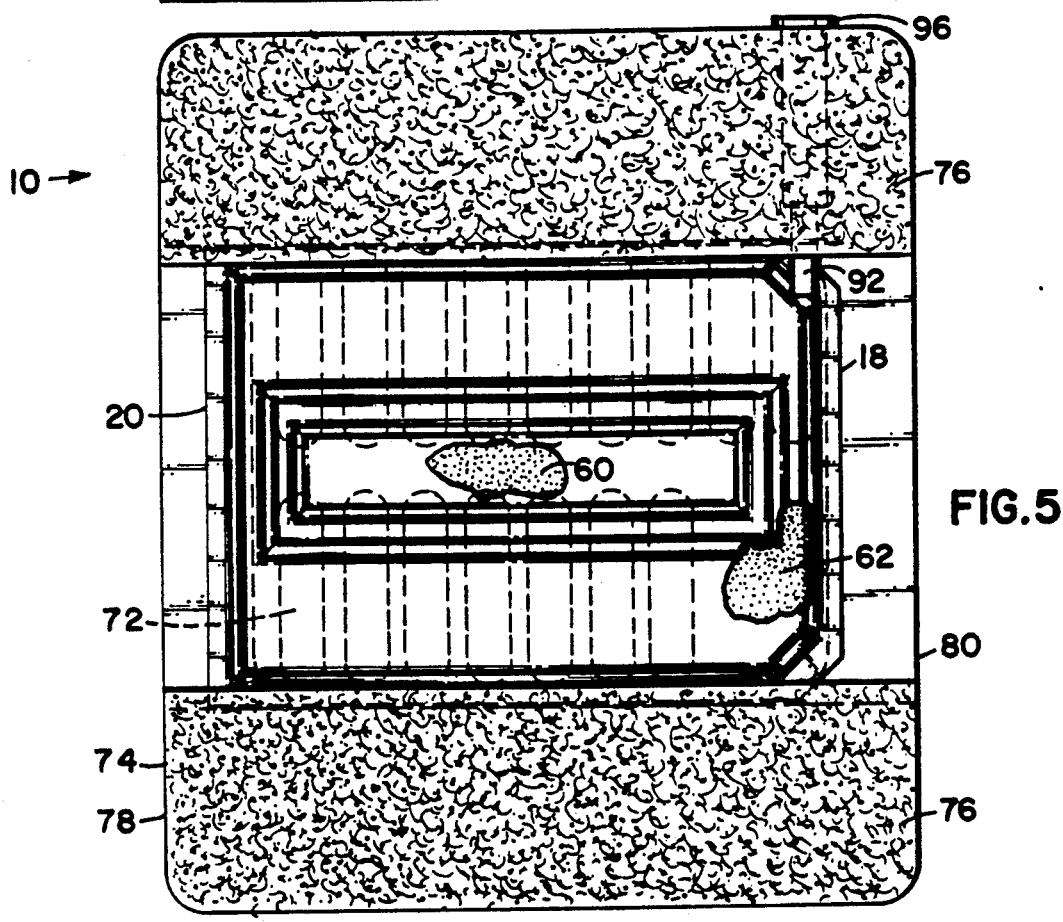
FIG. 5 is a rear view of the device of FIG. 1
Figure 6:
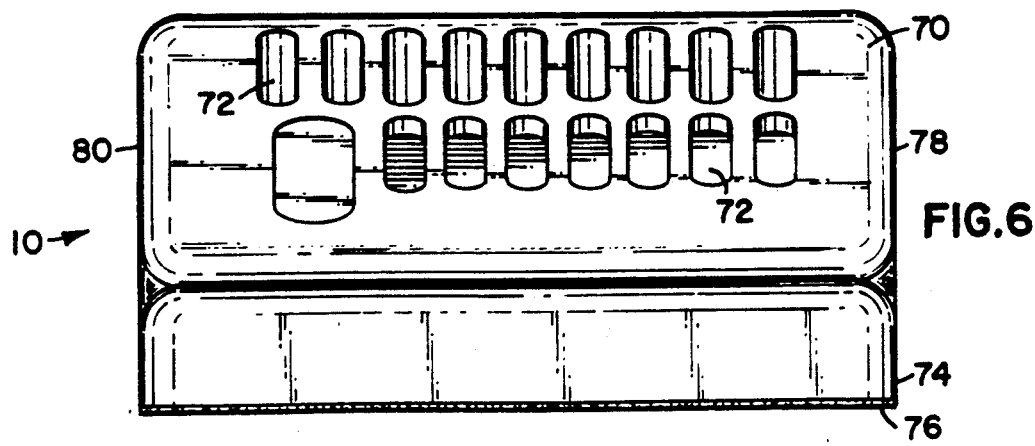
FIG. 6 is a right side elevational view of the device of FIG. 1.

After the user has removed the predetermined number of removable covers 68 to open the openings 64 and 66 exposing the fragrances 60 and 62 of cavities 26 and 28, the cartridge 12 is inserted into the slot 86 proximate the top member 78. The removal of a predetermined number of removable covers 68 to open the openings 64 and 66 to expose the fragrances 60 and 62 allows control of the rate of evaporation as well as the mixing of the fragrances 60 and 62. The cartridge 12 is inserted with the leading edge 18 entering the slot 86 first and the trailing edge 20 entering last. The cartridge 12 will be moved into the slot 86 until the stop 92 halts movement. The angled portion 22 of the leading edge 18 will rest on the stop 92. The air passage openings 72 receive air which moves over the cartridge 12 picking up the fragrances 60 and 62 and the air-fragrance mixture exits the air passage openings 72 thereby allowing dispersion of the fragrances 60 and 62. The passage of the air and fragrances 22 and 26 is shown by the arrows in FIGS. 1, 2, and 8.

When the cartridge 12 has expired, a new refill cartridge 98, which is identical to cartridge 12, must be inserted and the expired cartridge 12 must be removed. The new cartridge 98 is inserted, leading edge 18 first, into the slot 86 proximate the top member 78 and moved toward the bottom member 80. As shown in FIG. 7, the new cartridge 98 contacts the trailing edge 20 of the expired cartridge 12 and forces the angled portion 22 against the stop 92. The downward force on the new cartridge 98 is transmitted to the expired cartridge 12 and the stop 92 forces the spring 94 to compress, pushing the stop 92 into the cylindrical void 90 so that the cartridge 12 may exit the outer housing 14 proximate the bottom member 80. The angled portion 22 allows the force to push the stop 92 in while the cartridge moves down. Angled portions 22 and 24 are located on both sides of the cartridge 12 to accommodate a cartridge retainer 88 on either side of the outer housing 14. The user stops pushing the cartridge 98 down when the trailing edge 20 of the expired cartridge 12 passes the stop 92. After the cartridge 12 passes the stop 92 the spring 94 returns to an uncompressed state and provides retaining means for the refill cartridge 98. The angled portion 22 of the leading edge 18 of the refill cartridge 98 rests on the stop 92. The new cartridge 98 takes the place of the expired cartridge 12. Thus, the cartridge 12 is automatically dispensed and a replacement cartridge 98 is easily inserted.

It should be understood that cartridge 112 shown in FIG. 9 is utilized in the same manner as described above. The cartridge 112 is inserted into slot 86 proximate top member 78 with leading edge 119. Cover 137 is removed prior to insertion of the cartridge 112 to allow fragrances 60 and 62 to escape. The air passage openings 72 receive air which moves over the cartridge 112 picking up the fragrances 60 and 62 and the air fragrance mixture exits the air passage openings 72 thereby allowing dispersion of the fragrances 60 and 62. When the cartridge 112 has expired, a new refill cartridge is inserted in the manner shown in FIG. 7. The rounded corner of cartridge 112 and downward force to the refill cartridge depress stop 92 while the refill cartridge moves into place. Therefore, the cartridge 112 is automatically dispensed and replaced.

Other modifications of the invention will be apparent to those skilled in the art in light of the foregoing description. This description is intended to provide specific examples of individual embodiments which clearly disclose the present invention. Accordingly, the invention is not limited to those embodiments or the use of elements having specific configurations and shapes as presented herein. All alternative modifications and variations of the present invention which follow in the spirit and broad scope of the appended claims are included.

What is claimed is:

1. An air freshener device having a cartridge having a fragrance, comprising:
   (a) an outer housing defining a cavity for receiving the cartridge, the outer housing having a front member having air passage openings and a back member adapted and configured to be mounted on a surface, top and bottom members cooperatively connecting the front member to the back member, the top and bottom members having cartridge receiving openings, the cartridge receiving openings defining a slot, the slot extending the length of the outer housing;
   (b) the slot sized and configured to receive the cartridge whereby when the cartridge is expired a second cartridge is inserted into the slot proximate the top member and the second cartridge is moved in the slot toward the bottom member, the expired cartridge moves downward in the slot and is forced out the bottom member by movement of the second cartridge thereby refilling the outer housing; and
   (c) whereby the air passage openings receive air which moves over the cartridge picking up the fragrance resulting in an air-fragrance mixture which exits the air passage openings thereby allowing dispersion of the fragrance.

2. The air freshener device of claim 1 further comprising a cartridge retaining means cooperatively connected to the outer housing, the cartridge retaining means having a first and second position, wherein when in the first position the cartridge retaining means provides a stop for the cartridge, and is moveable to the second position by inserting the second cartridge into the slot proximate the top member and moving the second cartridge toward the bottom member, after the cartridge exits the outer housing the cartridge retaining means returns to the first position to retain the second cartridge.

3. The air freshener device of claim 2 wherein the cartridge retaining means includes a pin adjacent to and axially aligned with a spring, whereby force on the pin in the first position causes the spring to compress causing the pin to retract to the second position, and the cartridge to pass through the outer housing after which the spring is free to return to an uncompressed state and the pin returns to the first position thereby retaining the second cartridge.

4. The air freshener device of claim 3 wherein the back member includes a hole, wherein the hole houses the spring and the stop, the hole having one end capped by a plug.

5. An air freshener device comprising:
(a) an outer housing defining a cavity for receiving a cartridge having a fragrance, the outer housing having a front member having air passage openings and a back member adapted and configured to be mounted on a surface, top and bottom members cooperatively connecting the front member to the back member, the top and bottom members having cartridge receiving openings, the cartridge receiving openings defining a slot, the slot extending the length of the outer housing;
(b) the slot sized and configured to receive the cartridge whereby when the cartridge is expired a second cartridge is inserted into the slot proximate the top member and the second cartridge is moved in the slot toward the bottom member, the expired cartridge moves downward in the slot and is forced out the bottom member by movement of the second cartridge thereby refilling the housing; and
(c) whereby the air passage openings receive air which moves over the cartridge picking up the fragrance resulting in an air-fragrance mixture which exits the air passage openings thereby allowing dispersion of the fragrance;
(d) and wherein the cartridge comprises a housing, the housing having a sealed first cavity and a sealed second cavity;
(e) a first fragrance located within the first cavity, the first fragrance having a first volatility;
(f) a second fragrance located within the second cavity, the second fragrance having a second volatility;
(g) the first cavity having a first opening therein, the opening having a first removable cover;
(h) the second cavity having a second opening therein, the opening having a second removable cover; and
(i) whereby when the covers are removed the fragrances of first and second volatilities independently exit their respective cavities.

6. The cartridge of claim 5, wherein the cover for the first opening is separate from the cover for the second opening.

7. The device of claim 5, wherein the first removable cover and the second removable cover are a single removable cover.

8. An air freshener device, comprising:
(a) a cartridge having a fragrance;
(b) an outer housing defining a cavity for receiving the cartridge, the outer housing having a front member having air passage openings and a back member adapted and configured to be mounted on a surface, top and bottom members cooperatively connecting the front member to the back member, the top and bottom members having cartridge receiving openings, the cartridge receiving openings defining a slot, the slot extending the length of the outer housing;
(c) the slot sized and configured to receive the cartridge whereby when the cartridge is expired a second cartridge is inserted into the slot proximate the top member and the second cartridge is moved toward the bottom member, the expired cartridge is forced out the bottom member by movement of the second cartridge thereby refilling the outer housing; and
(d) whereby the air passage openings receive air which moves over the cartridge picking up the fragrance resulting in an air-fragrance mixture which exits the air passage openings thereby allowing dispersion of the fragrance.

9. The air freshener device of claim 8 wherein the cartridge has a housing having a sealed first cavity having a first fragrance of a first volatility and a sealed second cavity having a second fragrance of a second volatility, the first cavity having a first opening covered by a first removable cover and the second cavity having a second opening covered by a second removable cover whereby when the covers are removed the fragrances independently exit their respective cavities.

10. The cartridge of claim 9, wherein the cover for the first opening is separate from the cover for the second opening.

11. The device of claim 9, wherein the first removable cover and the second removable cover are a single removable cover.

12. A cartridge for an air freshener device, comprising:
(a) a housing, the housing having a sealed first cavity and a sealed second cavity wherein the first cavity is sized and configured to generally form a ring proximate the outer edges of the housing, the second cavity sized and configured to fit within the ring formed by the first cavity;
(b) a first fragrance located within the first cavity, the first fragrance having a first volatility;
(c) a second fragrance located within the second cavity, the second fragrance having a first volatility;
(d) the first cavity having a first opening therein, the opening having a first removable cover;
(e) the second cavity having a second opening therein, the opening having a second removable cover; and
(f) whereby when the covers are removed the fragrances of first and second volatilities independently exit their respective cavities.

13. The cartridge of claim 12 wherein the second cavity contains a greater volume of fragrance than the first cavity, the first fragrance having a first volatility lower than the second volatility of the second fragrance.

14. The cartridge of claim 12, wherein the cover for the first opening is separate from the cover for the second opening.

15. The cartridge of claim 12 wherein the rates of evaporation of the first and second fragrances are controlled by sizing the first and second openings thereby causing the fragrances to expire at approximately the same time.

16. The cartridge of claim 12 wherein the housing forms a single integral unit containing the first and second fragrances whereby when the covers are removed and the unit is inserted into the air freshener device the unit allows independent exiting of the first and second fragrances.

17. The cartridge of claim 12, wherein the first removable cover and the second removable cover are a single removable cover.

18. A cartridge for an air freshener device, comprising:
(a) a housing, the housing having a sealed first cavity and a sealed second cavity;
(b) a first fragrance located within the first cavity, the first fragrance having a first volatility;
(c) a second fragrance located within the second cavity, the second fragrances having a second volatility;
(d) the first cavity having a first opening therein, the opening having a first removable cover;
(e) the second cavity having a second opening therein, the opening having a second removable cover;
(f) the first and second openings having a plurality of generally circular openings each covered respectively by the removable covers, the first cavity having a greater plurality of openings than the second cavity, thereby allowing greater exposure of the fragrance of lower volatility and less exposure of the fragrance of higher volatility; and
(g) whereby when a predetermined number of openings are exposed by removing their respective covers, the fragrances within the first and second cavities may independently exit their respective cavities thereby equalizing the rate of evaporation of the fragrances.

19. The cartridge of claim 18 wherein the second cavity contains a greater volume of fragrance than the first cavity, the first fragrance having a first volatility lower than the second volatility of the second fragrance.

20. The cartridge of claim 18, wherein the cover for the first opening is separate from the cover for the second opening.

21. The cartridge of claim 13 wherein the rates of evaporation of the first and second fragrances are controlled by sizing of the first and second openings thereby causing the fragrances to expire at approximately the same time.

22. The cartridge of claim 18 wherein the housing forms a single integral unit containing the first and second fragrances whereby when the cover is removed and the unit is inserted into the air freshener device the unit allows independent exiting of the first and second fragrances.

23. An air freshener device, comprising:
(a) an outer housing defining a cavity for receiving a cartridge, the outer housing having a front member having air passage openings and a back member adapted and configured to be mounted on a surface, top and bottom members cooperatively connecting the front member to the back member, the top and bottom members having cartridge receiving openings, the cartridge receiving openings defining a slot, the slot extending the length of the outer housing;
(b) the slot sized and configured to receive the cartridge whereby when the cartridge is expired a second cartridge is inserted into the slot proximate the top member and the second cartridge is moved in the slot toward the bottom member, the expired cartridge moves downward in the slot and is forced out the bottom member by movement of the second cartridge thereby refilling the outer housing;
(c) whereby the air passage openings receive air which moves over the cartridge picking up the fragrance resulting in an air-fragrance mixture which exits the air passage openings thereby allowing dispersion of the fragrance;
(d) a cartridge retaining means cooperatively connected to the housing, the cartridge retaining means having a first and second position, wherein when in the first position the cartridge retaining means provides a stop for the cartridge, and is moveable to the second position by inserting the second cartridge into the slot proximate the top member and moving the second cartridge toward the bottom member, after the cartridge exits the outer housing the cartridge retaining means returns to the first position to retain the second cartridge; the cartridge retaining means including a pin adjacent to and axially aligned with a spring, whereby force on the pin in the first position causes the spring to compress causing the pin to retract to the second position, and the cartridge to pass through the outer housing after which the spring is free to return to an uncompressed state and the pin returns to the first position thereby retaining the second cartridge;
(e) the back member having a hole, wherein the hole houses the spring and the stop, the hole having one end capped by a plug;
(f) the cartridge having a housing having a sealed first cavity having a first fragrance of a first volatility and a sealed second cavity having a second fragrance of a second volatility, the first cavity having a first opening covered by a first removable cover and the second cavity having a second opening covered by a second removable cover whereby when the covers are removed the fragrances independently exit their respective cavities;
(g) the second cavity containing a greater volume of fragrance than the first cavity and the first fragrance having a first volatility lower than the second volatility of the second fragrance;
(h) the first cavity sized and configured to form a ring proximate the outer edges of the housing, the second cavity sized and configured to fit within the ring formed by the first cavity;
(i) whereby the rate of evaporation of the first and second fragrances are controlled by sizing of the first and second openings thereby causing the fragrances to expire at approximately the same time.

24. The device of claim 23, wherein the first removable cover and the second removable cover are a single removable cover.

* * * * *

UNITED STATES PATENT AND TRADEMARK OFFICE
CERTIFICATE OF CORRECTION

PATENT NO. : 5,050,798
DATED : September 24, 1991
INVENTOR(S) : Sullivan

It is certified that error appears in the above-identified patent and that said Letters Patent is hereby corrected as shown below:

In column 5, line 38, please delete "2 2/3" and substitute therefore --2 1/2--.

In column 6, line 31, please delete "Fraquance Inqredient" and substitute therefore --Fragrance Ingredient--.

In column 10, line 37, please delete "first" and substitute therefore --second--.

Signed and Sealed this

Thirtieth Day of March, 1993

Attest:

STEPHEN G. KUNIN

*Attesting Officer*  *Acting Commissioner of Patents and Trademarks*